US009138602B2

(12) United States Patent
Amalric et al.

(10) Patent No.: US 9,138,602 B2
(45) Date of Patent: Sep. 22, 2015

(54) POWDERY EMULSIFYING COMPOSITION OF ALKYL POLYGLYCOSIDES, USE THEREOF FOR PREPARING COSMETIC EMULSIONS, AND METHOD FOR PREPARING SAME

(71) Applicant: SOCIETE D'EXPLOITATION DE PRODUITS POUR LES INDUSTRIES CHIMIQUES SEPPIC, Paris (FR)

(72) Inventors: Chantal Amalric, Blan (FR); Alicia Roso, Saix (FR); Agnès Gorce, Marseilles (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

(21) Appl. No.: 14/278,746

(22) Filed: May 15, 2014

(65) Prior Publication Data

US 2014/0248368 A1  Sep. 4, 2014

Related U.S. Application Data

(62) Division of application No. 13/201,131, filed as application No. PCT/FR2010/050250 on Feb. 15, 2010, now Pat. No. 8,821,902.

(51) Int. Cl.
| | | |
|---|---|---|
| A61Q 19/00 | (2006.01) |
| A61K 8/92 | (2006.01) |
| A61K 8/34 | (2006.01) |
| A61K 8/60 | (2006.01) |
| A61K 8/02 | (2006.01) |
| B01F 17/00 | (2006.01) |
| A61Q 1/14 | (2006.01) |
| A61K 8/06 | (2006.01) |
| A61Q 19/04 | (2006.01) |
| A61Q 17/04 | (2006.01) |
| A61Q 1/02 | (2006.01) |

(52) U.S. Cl.
CPC ............ *A61Q 19/008* (2013.01); *A61K 8/022* (2013.01); *A61K 8/06* (2013.01); *A61K 8/062* (2013.01); *A61K 8/34* (2013.01); *A61K 8/342* (2013.01); *A61K 8/60* (2013.01); *A61K 8/602* (2013.01); *A61K 8/604* (2013.01); *A61K 8/92* (2013.01); *A61Q 1/14* (2013.01); *A61Q 17/04* (2013.01); *A61Q 19/00* (2013.01); *A61Q 19/007* (2013.01); *A61Q 19/04* (2013.01); *B01F 17/0092* (2013.01); *A61K 2800/412* (2013.01); *A61Q 1/02* (2013.01); *A61Q 19/005* (2013.01)

(58) Field of Classification Search
CPC ..... A61Q 19/008; A61Q 19/007; A61Q 1/14; A61Q 19/04; A61Q 19/00; A61Q 17/04; A61Q 19/005; A61Q 1/02; A61K 8/92; A61K 8/34; A61K 8/602; A61K 8/022; A61K 8/60; A61K 8/062; A61K 8/604; A61K 8/06; A61K 8/342; A61K 2800/412; B01F 17/0092

See application file for complete search history.

(56) References Cited

U.S. PATENT DOCUMENTS

| | | | |
|---|---|---|---|
| 5,670,471 | A | 9/1997 | Amalric et al. |
| 5,888,482 | A | 3/1999 | Amalric et al. |
| 5,958,431 | A | 9/1999 | Brancq et al. |
| 6,245,821 | B1 | 6/2001 | Bulcourt et al. |
| 6,268,400 | B1 | 7/2001 | Amalric et al. |
| 6,353,034 | B1 | 3/2002 | Amalric et al. |
| 6,488,946 | B1 | 12/2002 | Milius et al. |
| 6,723,774 | B2 | 4/2004 | Guntherberg et al. |
| 2003/0105169 | A1 | 6/2003 | Lennon |

FOREIGN PATENT DOCUMENTS

| | | |
|---|---|---|
| EP | 0992508 | 4/2000 |
| FR | 2756195 | 5/1998 |
| FR | 2784904 | 4/2000 |
| FR | 2830464 | 4/2003 |
| WO | 9206778 | 4/1992 |
| WO | 9513863 | 5/1995 |
| WO | 9637285 | 11/1996 |
| WO | 9637286 | 11/1996 |
| WO | 9718033 | 5/1997 |
| WO | 9847610 | 10/1998 |
| WO | 0056438 | 9/2000 |

OTHER PUBLICATIONS

Seppic, COSM'ethics, Mar. 2008, Seppic, pp. 1-33.
Machine Translation of EP0992508, WIPO, last accessed Sep. 20, 2013.
PharmaNews, A Fresh Shot of Inspiration, 2008, Alsiano, No. 8, pp. 1-10.
Snezana Savic et al., "Colloidal microstructure of binary systems and model creams stabilized with an alkylpolyglucoside non-ionic emulsifier", Colloid & Polymer Science; Kolloid-Zeitschrift und Zeitschrift fur Polymere, Springer, Berlin, DE, vol. 283, No. 4, Jan. 1, 2005, pp. 439-451, XP019340382, ISSN: 1435-1536.
International Search Report, dated Jun. 4, 2010, from corresponding PCT application.
French Search Report, dated Oct. 14, 2009, from corresponding French application.

*Primary Examiner* — Trevor Love
(74) *Attorney, Agent, or Firm* — Young & Thompson

(57) ABSTRACT

A powdery composition C1 contains for 100% of the mass: 5 to 70 mass % and more particularly 10 to 50 mass % of at least one compound of formula (I): $R—O-(G)_x-H$, wherein R is a linear saturated aliphatic radical including 12 to 22 carbon atoms, G is the remainder of a reducing sugar selected from the group including glucose, xylose and arabinose, and x is a decimal number greater than or equal to 1 and lower than or equal to 10; 95 to 30 mass % and more particularly 90 to 50 mass % of one or more alcohols of formula (II): $R'—OH$, wherein R' is a linear saturated aliphatic radical including 12 to 22 carbon atoms identical to or different from R as defined in formula (I), wherein at least 90 vol % of the particles have a diameter lower than or equal to 250 micrometers, more particularly a diameter lower than or equal to 150 micrometers.

6 Claims, No Drawings

POWDERY EMULSIFYING COMPOSITION OF ALKYL POLYGLYCOSIDES, USE THEREOF FOR PREPARING COSMETIC EMULSIONS, AND METHOD FOR PREPARING SAME

The invention relates to the provision of novel emulsifying compositions that can be used in the preparation of cosmetic and/or pharmaceutical formulations in particular for topical use.

Sugar-derived emulsifiers have been developed for more than about twenty years and their commercial success requires no further demonstration. They consist of a mixture of alkyl polyglycosides and/or alkenyl polyglycosides and of fatty alcohols, and are available on the market in solid form, whether as flakes, powder or beads. Such emulsifiers are described in the international applications published under numbers WO 92/06778, WO 95/13863, WO 96/37285, WO 98/47610 or FR 2784904. They make it possible to prepare stable emulsions in oil-in-water or water-in-oil form. The presence of an amount of fatty alcohols of greater than 30% by weight for 100% of the weight of these compositions creates a consistency and sensory properties which are advantageous, for instance a rich and creamy feel of the final emulsion.

Patent application FR 2 756 195 discloses emulsifying compositions intended for the preparation of emulsions with improved stability, and particularly intended for preparing stable fluid emulsions. These compositions comprise:

i) from 30% to 90% by weight of a mixture of at least one alkyl polyglycoside of which the linear or branched, saturated or unsaturated alkyl radical contains from 8 to 22 carbon atoms and at least one alkyl polyglycoside of which the alkyl radical is an oleyl radical or an isostearyl radical, and ii) from 10% to 70% by weight of at least one fatty alcohol of which the linear or branched, saturated or unsaturated alkyl radicals contain from 8 to 22 carbon atoms.

Application EP 0 992 508 discloses emulsifying compositions intended for improving the whiteness of the emulsions prepared, and which comprise:

i) from 5% to 60% by weight of a mixture of alkyl polyglycosides comprising, for 100% of its weight:
   from 30% to 95% by weight of a mixture of cetyl polyglycosides and stearyl polyglycosides,
   from 70% to 5% by weight of a mixture of arachidyl polyglycosides and behenyl polyglycosides;

ii) from 95% to 40% by weight of one or more fatty alcohols of which the linear or branched, saturated or unsaturated alkyl radicals contain from 14 to 22 carbon atoms.

The final emulsions are generally prepared by dispersion of these emulsifiers, either in water or in a polar phase, or in an oily phase. They are therefore preheated to a temperature above their melting point, which, according to the commercial compositions, is between 60 and 80° C., before being dispersed in the aqueous or oily phase of the final emulsion, which, in certain cases, constitutes an impairment to their commercial expansion since said final emulsions may also comprise thermosensitive and/or volatile ingredients. In addition, their use for producing oil-in-water emulsions is also impaired since they sometimes induce phase inversion, which results in an unwanted change in the direction of the final emulsion, to a water-in-oil emulsion.

In order to solve the problems linked to an emulsion preparation temperature that is too high, the aim has been to develop mixtures of alkyl polyglycosides and of fatty alcohols which are liquid at ordinary temperature, in order to avoid this melting operation during the preparation of the final emulsion. For this, branched or unsaturated fatty alcohols have been used to produce such mixtures. Such liquid emulsifiers are described in the international application published under number WO 00/56438 or else in the French patent application published under number FR 2 830 464. Such liquid compositions, owing to their very lipophilic nature, do not make it possible to prepare oil-in-water emulsions which are sufficiently stable and/or which have sensory properties that are sufficiently satisfactory for the final client.

In the context of their research on the constant improvement of emulsifiers for preparing "oil-in-water" emulsions which do not have the abovementioned drawbacks, the inventors have developed novel emulsifying compositions, and also a novel method for preparing oil-in-water emulsions, which make it possible to prepare emulsions that are stable in the presence of thermosensitive and/or volatile ingredients, without the appearance of phase inversion phenomena during their preparation, and which provide said emulsions with advantageous sensory properties, such as a rich and creamy feel.

According to a first aspect, the subject of the invention is a pulverulent composition C1 comprising, for 100% of its weight:

from 5% by weight to 70% by weight, more particularly from 10% by weight to 50% by weight, of at least one compound of formula (I):

$$R\text{—}O\text{-}(G)_x\text{-}H \quad (1)$$

in which the R radical represents a saturated linear aliphatic radical containing from 12 to 22 carbon atoms, G represents the residue of a reducing sugar selected from the group consisting of glucose, xylose and arabinose, and x represents a decimal number greater than or equal to 1 and less than or equal to 10;

from 95% by weight to 30% by weight, more particularly from 90% by weight to 50% by weight, of one or more alcohols of formula (II):

$$R'\text{—}OH \quad (II)$$

in which the R' radical, which may be identical to or different than the R radical as defined above, represents a saturated linear aliphatic radical containing from 12 to 22 carbon atoms, and in which at least 90% by volume of the particles have a diameter of less than or equal to 250 micrometers, and more particularly a diameter of less than or equal to 150 micrometers.

The expression "saturated linear aliphatic radical containing from 12 to 22 carbon atoms" denotes, in particular for R in formula (I) as defined above, for example dodecyl, tetradecyl, hexadecyl, octadecyl, eicosyl and docosyl radicals.

The expression "saturated linear aliphatic radical containing from 12 to 22 carbon atoms" denotes, in particular for R' in formula (II) as defined above, a radical which may be identical to or different than the R radical of formula (I) as defined above, for example dodecyl, tetradecyl, hexadecyl, octadecyl, eicosyl and docosyl radicals.

In formula (I) as defined above, x is a decimal number which represents the average degree of polymerization of the residue G.

When x is an integer, $(G)_x$ is the polymer residue of rank x of the residue G.

When x is a decimal number, formula (I) represents a mixture of compounds:

$$a_1R\text{—}O\text{-}(G)_1\text{-}H + a_2R\text{—}O\text{-}(G)_2\text{-}H + a_3R\text{—}O\text{-}(G)_3\text{-}H + \ldots + a_qR\text{—}O\text{-}(G)_q\text{-}H$$

with q representing an integer between 1 and 10 and in the molar proportions $a_1, a_2, a_3, \ldots a_q$ such that:

$$\sum_{q=10}^{q=1} a_q = 1; a_1 > 0$$

According to another particular aspect of the present invention, in formula (I) as defined above, x is between 1.05 and 5, and more particularly between 1.05 and 2.

The term "residue of a reducing sugar" denotes, for G in formula (I) as defined above, a residue of saccharide derivatives that do not contain in their structures a glycosidic bond established between an anomeric carbon and the oxygen of an acetal group as defined in the reference publication: "Biochemistry", Daniel Voet/Judith G. Voet, p. 250, John Wyley & Sons, 1990. The oligomeric structure $(G)_x$ may be in any isomeric form, whether it is a case of optical isomerism, geometric isomerism or positional isomerism; it may also represent mixtures of isomers.

In formula (I) as defined above, the R radical is linked to G via the anomeric carbon of the saccharide residue, so as to form an acetal function.

According to one particular aspect of the present invention, the term "residue of a reducing sugar" denotes, in formula (I) as defined above, the glucose residue.

According to another particular aspect of the present invention, the term "residue of a reducing sugar" denotes, in formula (I) as defined above, the xylose residue.

The expression: "the pulverulent composition C1 comprises at least 90% by volume of particles having a diameter of less than or equal to 250 micrometers, and more particularly a diameter of less than or equal to 150 micrometers" means, in the context of the present invention, that the pulverulent composition C1 is a powder of particles comparable to spheres, 90% by volume of which have a diameter of less than or equal to 250 micrometers, and more particularly less than or equal to 150 micrometers.

The determination of this parameter is carried out by means of a laser diffraction analyzer, for example the Malvern Mastersize™ 2000 laser particle sizer, equipped with a dispersing device, for example the MS1-Small Volume Sample Dispersion™ dispersing device, and connected to calculation software, which makes it possible to obtain a diffractogram consisting of a superposition of the diffraction images of each size of particles represented in the powder analyzed. In the analysis of the data thus collected, an initial size distribution is estimated and the theoretical diffractogram is calculated, and then compared with the real data recorded. The differences between the estimated data and the real data are then minimized using the least squares method. The software then calculates the distribution by volume as fundamental result and any other information is deduced from this result by assuming that the particles have a spherical shape.

This method of determination is particularly suitable for the characterization of powders which are made up of particles that are comparable to spheres having diameters of between 3000 micrometers and 0.1 micrometers, and for dry powders. The use of this type of method has particularly shown good results for particle sizes of greater than 10 micrometers [P. Bowen, "Particle Size Distribution Measurement from Millimeters to Nanometers and from Rods to Platelets"; J. Dispersion Science and Technology, 23(5), pp. 631-662 (2002)].

The preparation of the pulverulent composition C1 which is the subject of the present invention comprises:

a step A) of glycosylation of the alcohols of formula (II) as defined above, with a reducing sugar, as defined above, followed by a step B) of milling the products obtained in the form of solids at the end of step A).

The glycosylation reaction, carried out in step A), of the alcohols of formula (II) as defined above with a reducing sugar is well known to those skilled in the art and is described in the patent applications published under document numbers WO 92/06778, WO 96/37286, WO 95/13863, WO 98/47610 and FR 2784904. It is generally carried out in a reactor in the presence of an acidic catalytic system, with the stochiometric ratio between the two reactants being controlled, and with mechanical stirring under predetermined temperature and partial vacuum conditions, for example at a temperature of between 70° C. and 130° C. and under a partial vacuum of between 300 mbar ($3\times10^4$ Pa) and 20 mbar ($2\times10^3$ Pa).

The term "acidic catalytic system" denotes strong acids such as sulfuric acid, hydrochloric acid, phosphoric acid, nitric acid, hypophosphorous acid, methanesulfonic acid, para-toluenesulfonic acid, trifluoromethanesulfonic acid or ion-exchange resins. Such a glycosylation process can be supplemented and, if necessary or if desired, by neutralizing, filtering or discoloring operations.

The milling of the solid composition obtained at the end of step A) described above and which is in the form of an undivided solid, for instance in the form of beads or flakes, is carried out during step B) by means of a knife mill or by means of a device using the cyromilling micronization technique, so as to obtain, at the end of this milling step B), a pulverulent composition C1 which is the subject of the present invention.

The cryomilling micronization technique, consisting in freezing the solid composition resulting from step A), described above by means of liquid nitrogen or liquid carbon dioxide, before carrying out the milling operation, is preferentially chosen for preparing the pulverulent emulsifying composition C1 which is the subject of the present invention.

According to a more particular aspect, the pulverulent composition C1 which is the subject of the present invention comprises a non-zero proportion by weight of at least one compound of formula (Ia), corresponding to formula (I) as defined above in which R represents a saturated linear aliphatic radical containing from 20 to 22 carbon atoms, and a non-zero proportion by weight of at least one alcohol of formula (IIa), corresponding to formula (II) as defined above in which R' represents a saturated linear aliphatic radical containing from 20 to 22 carbon atoms.

According to another more particular aspect, the pulverulent composition C1 which is the subject of the present invention comprises, for 100% of its weight:

from 5% by weight to 20% by weight of at least one compound of formula (Ia);

from 1.5% by weight to 10% by weight of at least one compound of formula (Ib) corresponding to formula (I) as defined above, in which R represents a saturated linear aliphatic radical containing from 12 to 14 carbon atoms;

from 1% by weight to 10% by weight of at least one compound of formula (Ic) corresponding to formula (I) as defined above, in which R represents a saturated linear aliphatic radical containing from 16 to 18 carbon atoms;

from 45% by weight to 80% by weight of at least one compound of formula (IIa);

from 5% by weight to 10% by weight of at least one compound of formula (IIb) corresponding to formula (II) as defined above, in which R' represents a saturated linear aliphatic radical containing from 12 to 14 carbon atoms; and from 0% by weight to 10% by weight of at least one compound of formula (IIc) corresponding to formula (II) as defined above, in which R' represents a saturated linear aliphatic radical containing from 16 to 18 carbon atoms.

According to another more particular aspect, the pulverulent composition C1 which is the subject of the present invention comprises, for 100% of its weight:

from 5% by weight to 70% by weight of at least one compound of formula (Ic), and from 95% by weight to 30% by weight of at least one compound of formula (IIc).

According to another more particular aspect, the pulverulent composition C1 which is the subject of the present invention comprises at least 90% by volume of particles having a diameter of less than or equal to 100 micrometers, and more particularly a diameter of less than or equal to 50 micrometers.

According to another aspect, a subject of the invention is the use of a pulverulent composition C1 as described above, as an emulsifier for preparing emulsions. Said emulsions may be of oil-in-water type, water-in-oil type, water-in-oil-in-water type and oil-in-water-in-oil type, and said emulsions may be in the form of creams, milks, cream gels, fluid emulsions and vaporizable fluid emulsions.

In the context of the invention, the term "fluid emulsion" is intended to mean an emulsion of which the flow through a 6-millimeter ISO 2431 flow cup begins less than 5 seconds after removal of the stopper (test according to international standard ISO 2431). By way of fluid emulsions, mention may in particular be made of milks, in particular milks of the oil-in-water type, for cosmetic or hygiene use, such as makeup-removing milks, body milks, sun milks or self-tanning milks. By way of vaporizable fluid emulsions, mention may in particular be made of sprayable fluid emulsions comprising a cosmetically acceptable propellant gas.

According to another aspect, a subject of the invention is a method for preparing an oil-in-water cosmetic emulsion by emulsification of a fatty phase P1 with an aqueous phase P2, comprising at least a step a) of preparing said fatty phase P1 which comprises mixing at least one or more oils and/or one or more waxes, with an effective amount of the pulverulent composition C1, as defined above.

Surprisingly, owing to the fact that at least 90% by volume of the particles of the pulverulent composition C1 have a diameter of less than or equal to 250 micrometers, more particularly a diameter of less than or equal to 150 micrometers, more particularly a diameter of less than or equal to 100 micrometers and even more particularly less than or equal to 50 micrometers.

In the method which is the subject of the invention, step a) of preparing the fatty phase P1 by mixing one or more oils and/or one or more waxes with a pulverulent composition C1 as described above can be advantageously carried out at a temperature below the theoretical melting point of the pulverulent composition C1, at a temperature of less than or equal to 70° C., more particularly at a temperature of between 20° C. and 60° C., and even more particularly at a temperature of between 20° C. and 40° C.

Step a) of the method which is the subject of the invention can be carried out by means of any mixing device known to those skilled in the art, for example by means of a stirring device fitted with an "anchor" spindle, at stirring speeds of between 800 rpm and 1000 rpm, and for instance by means of a rotor-stator stirring device at stirring speeds of between 1000 rpm and 8000 rpm.

In the method as defined above, the expression "effective amount of pulverulent composition C1" is intended to mean a proportion by weight that is generally between 1% by weight and 10% by weight of the total weight of the emulsion.

In the method as defined above, among the constituent oils of the fatty phase P1 prepared during step a), mention may be made of:

volatile oils. The term "volatile oil" is intended to mean, in the present description, any oil which is capable of evaporating on contact with the skin and/or which has a low flashpoint, i.e. which has a flashpoint of less than approximately 100° C., and more particularly a flashpoint between 30° C. and 85° C. As volatile oil, mention may be made of branched-chain hydrocarbon-based oils preferably containing from 6 to 20 carbon atoms, for instance isoparaffins, isohexadecane, identified in Chemical Abstracts by the RN number=93685-80-4 and which is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9), and isododecane, and linear or cyclic, volatile silicone oils, such as cyclomethicones, for instance cyclohexadimethylsiloxane and cyclopentadimethylsiloxane;

mineral oils, such as liquid paraffin, liquid petroleum jelly, isoparaffins or white mineral oils;

oils of animal origin, such as squalene or squalane;

plant oils, such as phytosqualane, sweet almond oil, coconut oil, castor oil, jojoba oil, olive oil, rapeseed oil, groundnut oil, sunflower oil, wheatgerm oil, corn germ oil, soya oil, cottonseed oil, alfalfa oil, poppyseed oil, pumpkin oil, evening primrose oil, millet oil, barley oil, rye oil, safflower oil, candlenut oil, passion flower oil, hazelnut oil, palm oil, shea butter, apricot kernel oil, beauty leaf oil, sysymbrium oil, avocado oil, calendula oil, and oils derived from flowers or from vegetables;

ethoxylated plant oils;

synthetic oils, for instance fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, fatty acid monoglycerides, diglycerides and triglycerides, for instance glyceryl triheptanoate, alkyl benzoates, hydrogenated oils, poly-α-olefins, polyolefins such as polyisobutene, synthetic isoalkanes, hydrogenated polydecene or hydrogenated polyisobutene, sold in France by the company Ets B. Rossow et Cie under the name Parleam—Polysynlane™, mentioned in Michel and Irene Ash; Thesaurus of Chemical Products, Chemical Publishing Co, Inc. 1986 Volume 1, page 211 (ISBN 0 7131 3603 0), perfluoro oils; and silicone oils such as dimethylpolysiloxanes, methylphenylpolysiloxanes, silicones modified with amines, silicones modified with fatty acids, silicones modified with alcohols, silicones modified with alcohols and with fatty acids, silicones modified with polyether groups, epoxymodified silicones, silicones modified with fluoro groups, cyclic silicones and silicones modified with alkyl groups.

In the method as defined above, among the constituent waxes of the fatty phase P1 prepared during step a), mention may be made of beeswax, carnauba wax, candelilla wax, ouricury wax, Japan wax, cork fiber wax, sugar cane wax, paraffin waxes, lignite waxes, microcrystalline waxes, lanolin wax; ozokerite; polyethylene wax, silicone waxes; plant waxes; fatty alcohols and fatty acids which are solid at ambient temperature; glycerides which are solid at ambient temperature.

In the method which is the subject of the invention and as described above, the fatty phase P1 prepared during step a) may also comprise lipophilic and/or lipodispersible active agents, and more particularly temperature-sensitive lipophilic and/or lipodispersible active agents. Among the lipophilic and/or lipodispersible active agents that may be included in the fatty phase P1 prepared during step a) of the method which the subject of the invention, mention may be made of liposoluble and/or lipodispersible compounds which have a lightening or depigmenting action, a hydrating action, a tensioning action, a soothing or relaxing action, an anti-inflammatory action, a slimming action, a lipolytic action, a draining action, a detoxifying action, an energizing or decontracting action, a stimulant action, an emollient action, a neuromodulatory action, a protective action, a purifying, sebum-regulating or anti-hair loss action, an anti-aging action, or a firming, restructuring, free-radical-scavenging or antioxidant action. Such active ingredients are, for example, N-acylated proteins, N-acylated peptides, for instance Matrixil™, N-acylated amino acids, which are in their acid forms, for instance the N-(ω-undecylenoyl)phenylalanine sold by the company SEPPIC under the name Sepiwhite™ MSH, the N-octanoylglycine sold by the company SEPPIC under the name Lipacide™ C8G, the N-undecylenoylglycine sold by the company SEPPIC under the name Lipacide™ UG, partial hydrolysates of N-acylated proteins, amino acids, peptides, total hydrolysates of proteins, liposoluble vitamins, liposoluble vitamin derivatives, for instance retinol, vitamin E and its derivatives, lipids in general, lipids such as ceramides or phospholipids, active agents which have a slimming or lipolytic action, such as caffeine or its derivatives, panthenol and its derivatives, such as Sepicap™ MP, anti-aging active agents such as Sepilift™ DPHP or Lipacide™ PVB, active agents which increase the synthesis of extracellular matrix components, for example collagen, elastins and glycosaminoglycans, active agents which act favorably on chemical cell communication, such as cytokines, or physical cell communication, such as integrins, active agents which create a "hot" sensation on the skin, such as skin microcirculation activators (for example nicotinates) or products which create a feeling of "freshness" on the skin (for example menthol and derivatives thereof). Among the heat-sensitive liposoluble and/or lipodispersible active agents, mention may, for example, be made of vitamin E, vitamin E derivatives; essential oils recognized for their antiseptic actions, for instance *Thymus vulgaris*, for their anti-inflammatory actions, for instance *Syzygium aromaticum*, or for their healing and protective actions, for instance *Lavandulla officinalis*; fragrances; odorant and olfactory bases; carotene; vitamin A and derivatives thereof; polyunsaturated fatty acids; colorants.

According to one particular aspect, the method for preparing an oil-in-water emulsion which is the subject of the invention described above also comprises:
 at least one step b) of mixing the fatty phase P1 obtained at the end of step a), with an effective amount of a polyelectrolyte so as to obtain a phase P'1, then
 at least one step c) of emulsifying said phase P'1 obtained at the end of step b), with said aqueous phase P2.

The term "polyelectrolyte polymer" is intended to mean, in the present description, polymers comprising in their backbone at least one monomer comprising at least one ionic electrical charge associated with a counterion. Among the polyelectrolyte-type polymers that can be used in step b) of the method which is the subject of the invention, mention may be made of:
 homopolymers based on a monomer having a partially or totally salified strong acid function,
 homopolymers based on a monomer having a partially or totally salified weak acid function,
 homopolymers based on a cationic monomer,
 polymers based on at least one monomer having a partially or totally salified strong acid function, said monomer being polymerized:
  either with at least one monomer having a partially or totally salified weak acid function,
  or with at least one neutral monomer,
 polymers based on at least one cationic monomer polymerized with at least one neutral monomer,
 polymers based on at least one monomer having a partially or totally salified weak acid function, said monomer being polymerized:
  either with at least one monomer having a partially or totally salified weak acid function,
  or with at least one neutral monomer,
 polymers based on at least one monomer having a hydrophobic alkyl chain, polymerized with at least one monomer having a partially or totally salified weak acid function, and/or with at least one monomer having a partially or totally salified strong acid function, and/or with a neutral monomer.

In this context, the expression "partially or totally salified" means that the strong acid functions or weak acid functions are partially or totally salified in the form, in particular, of alkali metal salts, such as the sodium salt or the potassium salt, of an ammonium salt or of an amino alcohol salt, for instance the monoethanolamine salt.

The strong acid function of the monomer may in particular be the sulfonic acid function or the phosphonic acid function, said functions being partially or totally salified. Said monomer will be advantageously selected from styrenesulfonic acid or 2-sulfoethyl methacrylate, or styrenephosphonic acid, partially or totally salified, or 2-methyl-[(1-oxo-2-propenyl)amino]-1-propanesulfonic acid (AMPS), partially or totally salified, in sodium salt, potassium salt, ammonium salt or monoethanolamine salt form.

The weak acid function of the monomer may in particular be the partially or totally salified carboxylic acid function. Said monomer may be especially selected from acrylic acid, methacrylic acid, itaconic acid or maleic acid partially or totally salified in sodium salt, potassium salt, ammonium salt or monoethanolamine salt form.

When the polymer is a copolymer based on a monomer having a partially or totally salified strong acid function, copolymerized with at least one neutral monomer, said neutral monomer is selected from acrylamide, methacrylamide, vinylpyrrolidone, N,N-dimethylacrylamide, 2-hydroxyethyl acrylate, 2-hydroxyethyl methacrylate, 2,3-dihydroxypropyl methacrylate or an ethoxylated derivative, having a molecular weight of between 400 and 1000, of each of these hydroxylated esters, tris(hydroxymethyl)acrylamidomethane or tris(hydroxymethyl)methacrylamidomethane or an ethoxylated derivative, having a molecular weight of between 400 and 1500, of these amides.

The polyelectrolyte polymers described above may be "branched" or "crosslinked". The term "branched polymer" denotes a nonlinear polymer which has pendant chains so as to obtain, when this polymer is dissolved in water, a high state of entanglement, resulting in very high low-gradient viscosities. The term "crosslinked polymer" denotes a nonlinear polymer existing in the water-insoluble but water-swellable three-dimensional network state and thus resulting in the production of a chemical gel.

When the polymer is crosslinked and/or branched, the crosslinking agent and/or the branching agent is in particular selected from diethylene compounds and polyethylene compounds, and most particularly from diallyloxyacetic acid or a salt thereof, and in particular the sodium salt thereof, triallylamine, trimethylolpropane triacrylate, ethylene glycol dimethacrylate, diethylene glycol diacrylate, diallylurea or methylene(bis)acrylamide.

The crosslinking and/or branching agent is generally used in a molar proportion, expressed relative to the monomers used, of from 0.005 mol % to 1 mol %, preferably from 0.01 mol % to 0.2 mol %, and even more preferentially from 0.01 mol % to 0.1 mol %.

Among the polyelectrolyte-type polymers which are most particularly suitable for carrying out step b) of the method which is the subject of the invention, mention may be made of copolymers of partially or totally salified acrylic acid and of partially or totally salified 2-methyl-[(1-oxo-2-propenyl)amino]-1-propanesulfonic acid (AMPS), copolymers of acrylamide and of partially or totally salified 2-methyl-[(1-oxo-2-propenyl)amino]-1-propanesulfonic acid (AMPS), copolymers of 2-hydroxyethyl acrylate and of partially or totally salified 2-methyl-[(1-oxo-2-propenyl)amino]-1-propanesulfonic acid (AMPS), the homopolymer of partially or totally salified acrylic acid, the homopolymer of partially or totally salified 2-methyl-[(1-oxo-2-propenyl)amino]-1-propanesulfonic acid (AMPS), copolymers of acryloylethyltrimethylammonium chloride and of acrylamide, copolymers of AMPS and of vinylpyrrolidone, and copolymers of acrylic acid and of alkyl acrylates in which the carbon-based chain contains between ten and thirty carbon atoms.

Such polymers are obtained by preparation methods known to those skilled in the art, among which mention may be made of suspension polymerization methods, methods of precipitation polymerization in the presence of a solvent, inverse suspension polymerization methods and reverse-phase polymerization methods.

Such polyelectrolyte polymers are in the form of powders, suspensions, emulsions or inverse emulsions.

Such polyelectrolyte polymers are sold under the names Simulgel™ EG, Sepigel™ 305, Simulgel™ NS, Simulgel™ 800, Simulgel™ A, Simulgel™ EPG, Simulgel™ INS, Simulgel™ FL, Simulgel™ SMS 88, Sepigel™ 501, Sepigel™ 502, Sepiplus™ 250, Sepiplus™ 265, Sepiplus™ 400, Sepiplus™ S, Sepinov™ EMT 10, Carbopol™, Ultrez™ 10, Aculyn™, Pemulen™ TR1, Pemulen™ TR2, Luvigel™ EM, Salcare™ SC91, Salcare™ SC92, Salcare™ SC95, Salcare™ SC96, Flocare™ ET100, Flocare™ ET58, Hispagel™, Novemer™ EC1, Aristoflex™ AVC, Aristoflex™ HBM, Rapithix™ A60, Rapithix™ A100, Cosmedia™ SP and Stabileze™ 06.

The expression "effective amount of polyelectrolyte polymer" signifies that the dry weight of said polyelectrolyte polymer constitutes between 0.1% by weight and 4% by weight, preferably between 0.5% by weight and 2% by weight, for 100% of the weight of the fatty phase P'1 prepared in step b) of the method which is the subject of the invention, if such a polyelectrolyte polymer results from a precipitation polymerization method.

The dry weight of said polyelectrolyte polymer constitutes between 0.25% by weight and 4% by weight, preferably between 0.5% by weight and 2% by weight, for 100% of the weight of the fatty phase P'1 prepared in step b) of the method which is the subject of the invention, if such a polyelectrolyte polymer results from an inverse emulsion polymerization method.

The expression "cosmetically acceptable" used in the definition of the aqueous phase employed during step c) of the method for preparing an oil-in-water cosmetic emulsion which is the subject of the invention describes, according to European Economic Community Council Directive No. 76/768/EEC of Jul. 27, 1976, amended by directive No. 93/35/EEC of Jun. 14, 1993, any substance or preparation intended to be brought into contact with the various parts of the human body (epidermis, body hair and head hair system, nails, lips and genital organs) or with the teeth or the oral mucosac, for the purpose, exclusively and principally, of cleaning them, of fragrancing them, of modifying the appearance thereof and/or of correcting body odors thereof and/or of protecting them or of maintaining them in good condition. A cosmetically acceptable aqueous phase conventionally contains water, one or more cosmetically acceptable organic solvents, or a mixture of water and one or more organic solvents. The cosmetically acceptable solvents may more particularly be selected from polyhydric alcohols, for instance glycerol, diglycercol, glycerol oligomers, ethylene glycol, propylene glycol, butylene glycol, hexylene glycol, diethylene glycol, xylitol, erythritol or sorbitol, or water-soluble alcohols such as ethanol, isopropanol or butanol.

In the method which is the subject of the invention and as described above, the cosmetically acceptable aqueous phase P2 may also comprise water-soluble and/or water-dispersible active agents, and more particularly temperature-sensitive water-soluble and/or water-dispersible active agents. Among the water-soluble and/or water-dispersible active agents that may be included in the cosmetically acceptable aqueous phase P2, mention may be made of water-soluble and/or water-dispersible compounds which have a lightening or depigmenting action, a hydrating action, a tensioning action, a soothing or relaxing action, an anti-inflammatory action, a slimming action, a lipolytic action, a draining action, a detoxifying action, an energizing or decontracting action, a stimulant action, an emollient action, a neuromodulatory action, a protective action, a purifying, sebum-regulating or anti-hair loss action, an anti-aging action, or a firming, restructuring, free-radical-scavenging or antioxidant action. Such active ingredients are, for example, water-soluble and/or water-dispersible vitamins, for instance vitamin C and derivatives thereof, magnesium ascorbyl phosphate and derivatives thereof, ascorbyl glucoside, phytic acid, fruit acids, aqueous or aqueous-alcoholic or aqueous-glycolic extracts of polyphenols, of quinoa, of parsnip, of potentilla, of grape, of wine, olive extracts, grape-cake extracts, polyols (for example glycerol or butylene glycol), milk derivatives, or the various components that go to make up the composition of NMF (natural moisturizing factor), for example urea, pyrrolidonecarboxylic acid or derivatives of this acid, amino acids, mineral salts, sugars or sugar derivatives, polysaccharides or derivatives thereof, hydroxy acids, for example lactic acid, aqueous or aqueous-alcoholic or aqueous-glycolic plant extracts, such as tannin-rich plant extracts, isoflavon-rich plant extracts or terpene-rich plant extracts, extracts of fresh water or marine algae, marine extracts in general, such as corals, bacterial extracts; minerals, such as Givobio™, calcium derivatives, magnesium derivatives, copper derivatives, cobalt derivatives, zinc derivatives, lithium derivatives or manganese derivatives, silver salts or gold salts; active agents which have an energizing or stimulant property, such as Sepitonic™ M3 or Physiogenyl™; self-tanning active agents, for example dihydroxyacetone and erythrulose; active agents which moisturize or restructure the epidermis, for instance Aquaxyl™, N-acylated amino acids which are in their salified forms, for instance the sodium or potassium or ammonium or amino alcohol salts of N-(ω-undecylenoyl)phenylalanine, of octanoylglycine or of undecylenoylglycine, the salts of N-acylated protein partial hydrolysates, amino acids, and total protein hydrolysates. Among the heat-sensitive water-soluble and/or water-dispersible active agents, mention may, for example, be made of self-tanning active agents, for instance dihydroxyacetone and erythrulose; honey; floral waters, for instance barley water made from the young shoots of the plant; vitamin C and derivatives thereof; aqueous hydrogen peroxide.

Surprisingly, owing to the fact that at least 90% by volume of the particles of the pulverulent emulsifying composition C1 have a diameter of less than or equal to 250 micrometers, more particularly a diameter of less than or equal to 150 micrometers, more particularly a diameter of less than or equal to 100 micrometers and even more particularly less than or equal to 50 micrometers, In the method which is the subject of the invention, step c) of mixing the phase P'1 obtained at the end of step b) with the cosmetically acceptable aqueous phase P2 can be advantageously carried out at a temperature of less than or equal to 70° C., more particularly at a temperature of between 20° C. and 60° C., and even more particularly at a temperature of between 20° C. and 40° C.

Step c) of the method which is the subject of the invention can be carried out by means of any mixing device known to those skilled in the art, for instance by means of a stirring device fitted with an "anchor" spindle, at stirring speeds of between 80 rpm and 1000 rpm, and for instance by means of a rotor-stator stirring device at stirring speeds of between 1000 rpm and 8000 rpm.

According to one particular aspect of the invention, a variant of the method for preparing an oil-in-water cosmetic emulsion as defined above comprises at least one step b' of emulsifying said fatty phase P' obtained in step a), with said polyelectrolyte polymer and said aqueous phase P2.

Surprisingly, owing to the fact that at least 90% by volume of the particles of the pulverulent emulsifying composition C1 have a diameter of less than or equal to 250 micrometers, more particularly a diameter of less than or equal to 150 micrometers, more particularly a diameter of less than or equal to 100 micrometers and even more particularly less than or equal to 50 micrometers, in the variant of the method which is the subject of the invention, step b') of mixing the fatty phase P1 obtained at the end of step a), with a polyelectrolyte polymer as described above and with an aqueous phase P2 as described above, can be advantageously carried out at a temperature of less than 70° C., more particularly at a temperature of between 20° C. and 60° C., and even more particularly at a temperature of between 20° C. and 40° C.

Step b') of the variant of the method which is the subject of the invention can be carried out by means of any mixing device known to those skilled in the art, for instance by means of a stirring device fitted with an "anchor" spindle, at stirring speeds of between 80 rpm and 1000 rpm, and for instance by means of a rotor-stator stirring device at stirring speeds of between 1000 rpm and 8000 rpm.

According to another aspect, a subject of the invention is a method for preparing an oil-in-water cosmetic emulsion by emulsification of a fatty phase with an aqueous phase D1 with a fatty phase D2, comprising a step a1) of preparing said aqueous phase D1 which comprises mixing an effective amount of the pulverulent emulsifying composition C1, as defined in one of claims 1 to 5, with water or an aqueous dispersion of one or more cosmetically acceptable hydrophilic ingredients.

The term "cosmetically acceptable hydrophilic ingredients" is intended to mean, for example, the water-soluble and/or water-dispersible active agents as described above, and more particularly temperature-sensitive water-soluble and/or water-dispersible active agents as described above.

Step a1) of the method which is the subject of the invention can be carried out by means of any mixing device known to those skilled in the art, for instance by means of a stirring device fitted with an "anchor" spindle, at stirring speeds of between 80 rpm and 1000 rpm, and for instance by means of a rotor-stator stirring device at stirring speeds of between 1000 rpm and 8000 rpm.

Surprisingly, owing to the fact that at least 90% by volume of the particles of the pulverulent emulsifying composition C1 have a diameter of less than or equal to 250 micrometers, more particularly a diameter of less than or equal to 150 micrometers, more particularly a diameter of less than or equal to 100 micrometers and even more particularly less than or equal to 50 micrometers, In the method which is the subject of the invention, step a1) of preparing the dispersion D1 by mixing the pulverulent emulsifying composition C1 as defined above, with the cosmetically acceptable aqueous phase, can be advantageously carried out at a temperature of less than or equal to 70° C., more particularly at a temperature of between 20° C. and 60° C., and even more particularly at a temperature of between 20° C. and 40° C.

According to one particular aspect, the method for preparing an oil-in-water emulsion which is the subject of the invention described above also comprises:
  a step b1) of preparing said fatty phase D2 which comprises mixing at least one or more oils and/or one or more waxes, with an effective amount of a polyelectrolyte polymer;
  a step c1) of mixing said fatty phase D2 obtained at the end of step b1), with said aqueous phase D1 obtained at the end of step a1).

The fatty phase D2 may also comprise liposoluble and/or lipodispersible active agents as described above, and more particularly temperature-sensitive liposoluble and/or lipodispersible active agents as described above.

Surprisingly, owing to the fact that at least 90% by volume of the particles of the pulverulent emulsifying composition C1 have a diameter of less than or equal to 250 micrometers, more particularly a diameter of less than or equal to 150 micrometers, more particularly a diameter of less than or equal to 100 micrometers and even more particularly less than or equal to 50 micrometers, in the method which is the subject of the invention, step c1) of preparing the dispersion D1 by mixing the pulverulent emulsifying composition C1 as defined above, with the cosmetically acceptable aqueous phase, can be advantageously carried out at a temperature of less than or equal to 70° C., more particularly at a temperature of between 20° C. and 60° C., and even more particularly at a temperature of between 20° C. and 40° C.

Step c1) of the method which is the subject of the invention can be carried out by means of any mixing device known to those skilled in the art, for instance by means of a stirring device fitted with an "anchor" spindle, at stirring speeds of between 80 rpm and 1000 rpm, and for instance by means of a rotor-stator stirring device at stirring speeds of between 1000 rpm and 8000 rpm.

According to another aspect, a subject of the invention is a preparation for topical use comprising an oil-in-water emulsion prepared according to the methods and variants thereof described above.

The expression "for topical use" used in the definition of the preparation which is the subject of the invention means that said preparation is used by application to the skin, the hair, the scalp or the mucous membranes, whether it is a direct application in the case of a cosmetic, dermocosmetic, dermopharmaceutical or pharmaceutical composition, or an indirect application, for example in the case of a bodycare product in the form of a textile or paper wipe, or of sanitary products intended to come into contact with the skin or mucous membranes.

The preparations for topical use, comprising an oil-in-water emulsion prepared according to the methods and variants thereof described above, and which are subjects of the present invention, may be in the form of creams, milks, cream gels, fluid lotions or vaporizable fluid lotions.

Generally, these preparations for topical use, comprising an oil-in-water emulsion prepared according to the methods and variants thereof described above, and which is a subject of the present invention, also comprise excipients and/or active ingredients normally used in the field of formulations for topical use, in particular cosmetic, dermocosmetic, pharmaceutical or dermopharmaceutical formulations, such as thickening and/or gelling surfactants, stabilizers, film-forming compounds, hydrotropic agents, plasticizers, emulsifiers and co-emulsifiers, opacifiers, pearlescent agents, overfatting agents, sequestering agents, chelating agents, antioxidants, fragrances, preservatives, conditioning agents, bleaching agents intended for bleaching bodily hairs and the skin, active ingredients intended to provide a treating action with respect to the skin or the hair, sunscreens, mineral fillers or pigments, particles providing a visual effect or intended for the encapsulation of active agents, exfoliant particles and texture agents.

As examples of thickening and/or gelling surfactants optionally present in the preparation for topical use, comprising an oil-in-water emulsion prepared according to the methods and variants thereof described above, and which is a subject of the present invention, mention may be made of:

- optionally alkoxylated alkyl polyglycoside fatty esters, and most particularly ethoxylated methylpolyglucoside esters, such as PEG 120 methyl glucose trioleate and PEG 120 methyl glucose dioleate, sold respectively under the names Glucamate™ LT and Glumate™ DOE120;
- alkoxylated fatty esters, such as the PEG 150 pentaerythrytyl tetrastearate sold under the name Crothix™ DS53, and the PEG 55 propylene glycol oleate sold under the name Antil™ 141;
- fatty-chain polyalkylene glycol carbamates, such as the PPG 14 laureth isophoryl dicarbamate sold under the name Elfacos™ T211, and the PPG 14 palmeth 60 hexyl dicarbamate sold under the name Elfacos™ GT2125.

As examples of opacifiers and/or pearlescent agents optionally present in the preparation for topical use, comprising an oil-in-water emulsion prepared according to the methods and variants thereof described above, and which is a subject of the present invention, mention may be made of sodium palmitates or stearates or hydroxystearates, magnesium palmitates or stearates or hydroxystearates, ethylene glycol monostearates or distearates, polyethylene glycol monostearates or distearates, fatty alcohols, and styrene homopolymers and copolymers, such as the styrene acrylate copolymer sold under the name Montopol™ OP1 by the company SEPPIC.

As examples of texture agents optionally present in the preparation for topical use, comprising an oil-in-water emulsion prepared according to the methods and variants thereof described above, and which is a subject of the present invention, mention may be made of N-acylated derivatives of amino acids, such as lauroyllysine sold under the name Aminohope™ LL by the company Ajinomoto, the polymethyl methacrylates sold under the name Micropearl™ by the company SEPPIC, and nylon-12.

As examples of sunscreens optionally present in the preparation for topical use, comprising an oil-in-water emulsion prepared according to the methods and variants thereof described above, and which is a subject of the present invention, mention may be made of those which appear in amended cosmetic directive 76/768/EEC, annex VII.

The following examples illustrate the invention without, however, limiting it.

EXAMPLE 1

Preparation of Pulverulent Emulsifying Compositions which are Subjects of the Invention

EXAMPLE 1.1

Preparation of a Pulverulent Emulsifying Composition (X) Consisting of Arachidyl Alcohol, Benhenyl Alcohol, Arachidyl Polyglucosides and Behenyl Polyglucoside 950.0 g of a mixture of arachidyl alcohol and behenyl alcohol, in a 70/30 arachidyl alcohol/behenyl alcohol weight ratio, are placed in a jacketed glass reactor, in which a heat-transfer fluid circulates, and which is equipped with efficient stirring, at a temperature of 80° C. so as to allow the complete melting of the mixture of alcohols. 97.5 g of anhydrous glucose are then added gradually to the reaction medium so as to allow homogeneous dispersion thereof. The homogeneous mixture is maintained at a temperature of 80° C. for 30 minutes, and then 1.43 g of 98% sulfuric acid and 0.95 g of 50% hypophosphorous acid are introduced into the previously prepared homogeneous dispersion. The reaction medium is placed under a partial vacuum of 90 mbar to 45 mbar, and maintained at a temperature of 100° C.-105° C. for a period of 5 hours, with evacuation of the water formed by means of a distillation apparatus. The reaction medium is then cooled to 85° C.-90° C. and neutralized by adding 1.3 g of 40% sodium hydroxide, so as to bring the pH of a 5% solution of this mixture to a value of approximately 6.5. The composition thus obtained is then emptied out at a temperature of 70° C. and maintained at ambient temperature so as to obtain an undivided homogeneous solid (composition $X_1$).

The composition ($X_1$) obtained in the preceding step in the form of an undivided homogeneous solid is then milled by means of a Micronis cryomilling device, equipped with liquid nitrogen cooling and a twin-rotor pin mill operating at a frequency of 60 Hz, so as to obtain a composition (X) which is in the form of a fine powder, the analytical characteristics of which are collated in table 1 below.

EXAMPLE 1.2

Preparation of a Pulverulent Emulsifying Composition (Y) Consisting of Cetyl Alcohol, Stearyl Alcohol, Cetyl Polyglucosides and Stearyl Polyglucoside 952.0 g of a mixture of cetyl alcohol and stearyl alcohol, in a 50/50 cetyl alcohol/stearyl alcohol weight ratio, are placed in a jacketed glass reactor, in which a heat-transfer fluid circulates, and which is equipped with efficient stirring, at a temperature of 80° C. so as to allow complete melting of the mixture of alcohols. 125.0 g of anhydrous glucose are then added gradually to the reaction medium so as to allow homogeneous dispersion thereof. The homogeneous mixture is maintained at a temperature of 80° C. for 30 minutes, and then 1.12 g of 98% sulfuric acid and 0.86 g of 50% hypophosphorous acid are introduced into the previously prepared homogeneous dispersion. The reaction medium is placed under a partial vacuum of 90 mbar to 45 mbar, and maintained at a temperature of 100° C.-105° C. for a period of 5 hours, with evacuation of the water formed by means of a distillation apparatus. The reaction medium is then cooled to 85° C.-90° C. and neutralized by adding 1.3 g of 40% sodium hydroxide, so as to bring the pH of a 5% solution of this mixture to a value of approximately 6.5. The composition thus obtained is then emptied out at a temperature of 70° C. and maintained at ambient temperature so as to obtain a homogeneous solid (composition $Y_1$).

The composition ($Y_1$) obtained in the preceding step in the form of a homogeneous solid is then milled by means of a Micronis cryomilling device, equipped with liquid nitrogen cooling and a twin-rotor pin mill operating at a frequency of 60 Hz, so as to obtain a composition (Y) which is in the form of a fine powder, the analytical characteristics of which are collated in table 1 below.

EXAMPLE 1.3

Preparation of a Pulverulent Emulsifying Composition ($Y_2$) Consisting of Cetyl Alcohol, Stearyl Alcohol, Cetyl Polyglucosides and Stearyl Polyglucoside 952.0 g of a mixture of cetyl alcohol and stearyl alcohol, in a 50/50 cetyl alcohol/stearyl alcohol weight ratio, are placed in a jacketed glass reactor, in which a heat-transfer fluid circulates, and which is equipped with efficient stirring, at a temperature of 80° C. so as to allow complete melting of the mixture of alcohols. 125.0 g of anhydrous glucose are then added gradually to the reaction medium so as to allow homogeneous dispersion thereof. The homogeneous mixture is maintained at a temperature of 80° C. for 30 minutes, and then 1.12 g of 98% sulfuric acid and 0.86 g of 50% hypophosphorous acid are introduced into the previously prepared homogeneous dispersion. The reaction medium is placed under a partial vacuum of 90 mbar to 45 mbar, and maintained at a temperature of 100° C.-105° C. for a period of 5 hours, with evacuation of the water formed by means of a distillation apparatus. The reaction medium is then cooled to 85° C.-90° C. and neutralized by adding 1.3 g of 40% sodium hydroxide, so as to bring the pH of a 5% solution of this mixture to a value of approximately 6.5. The reaction medium thus neutralized is then introduced into a thin film evaporator, under a reduced pressure of 3 to 5 mbar and with a wall temperature of 210° C., so as to distill-off a part of the residual cetyl and stearyl alcohols. The distillation pellet is then emptied out and cooled to ambient temperature so as to obtain a composition ($Y'_2$) which is in the form of a homogeneous solid. The composition ($Y'_2$) obtained in the preceding step in the form of a homogeneous solid is then milled by means of a Micronis cryomilling device, equipped with liquid nitrogen cooling and a twin-rotor pin mill operating at a frequency of 60 Hz, so as to obtain a composition ($Y_2$) which is in the form of a fine powder, the analytical characteristics of which are collated in table 1 below.

EXAMPLE 1.4

Preparation of a Pulverulent Emulsifying Composition (W) Consisting of Lauryl Alcohol, Myristyl Alcohol, Cetyl Alcohol, Stearyl Alcohol, Arachidyl Alcohol, Behenyl Alcohol, Lauryl Polyglucosides, Myristyl Polyglucosides, Cetyl Polyglucosides, Stearyl Polyglucoside, Arachidyl Polyglucoside and Behenyl Polyglucosides 955.0 g of a mixture of alcohols consisting, as percentage by weight, of 16.5% of lauryl alcohol, 18.5% of myristyl alcohol, 4.5% of a mixture of cetyl alcohol and stearyl alcohol in a 50/50 cetyl alcohol/stearyl alcohol weight ratio, and 60.5% of a mixture of arachidyl alcohol and behenyl alcohol, in a 70/30 arachidyl alcohol/behenyl alcohol weight ratio, are placed in a jacketed glass reactor, in which a heat-transfer fluid circulates, and which is equipped with efficient stirring, at a temperature of 80° C., so as to allow complete melting of the mixture of alcohols. The amount of glucose necessary for the molar ratio between the mixture of fatty alcohols and the glucose to be 6/1 is then gradually added to this mixture of alcohols.

The homogeneous mixture is maintained at a temperature of 80° C. for 30 minutes, and then 1.23 g of 98% sulfuric acid and 0.92 g of 50% hypophosphorous acid are introduced into the previously prepared homogeneous dispersion. The reaction medium is placed under a partial vacuum of 90 mbar to 45 mbar, and maintained at a temperature of 100° C. to 105° C. for a period of 5 hours, with evacuation of the water formed by means of a distillation apparatus. The reaction medium is then cooled to 85° C.-90° C. and neutralized by adding 1.6 g of 40% sodium hydroxide, so as to bring the pH of a 5% solution of this mixture to a value of approximately 6.5. The composition thus obtained is then emptied out at a temperature of 70° C. and maintained at ambient temperature so as to obtain a homogeneous solid (composition $W_1$).

The composition ($W_1$) obtained in the preceding step in the form of a homogeneous solid is then milled by means of a Micronis cryomilling device, equipped with liquid nitrogen cooling and a twin-rotor pin mill operating at a frequency of 60 Hz, so as to obtain a composition (W) which is in the form of a fine powder, the analytical characteristics of which are collated in table 1 below.

COMPARATIVE EXAMPLE 1.5

Preparation of a Solid Composition ($X_1$) Consisting of Arachidyl Alcohol, Behenyl Alcohol, Arachidyl Polyglucosides and Behenyl Polyglucoside The preparation method described in example 1.1 is carried out until the composition ($X_1$) which is in the form of a nonpulverulent solid is obtained; the milling step is not performed. The analytical characteristics of the composition ($X_1$) are indicated in table 1 below.

COMPARATIVE EXAMPLE 1.6

Preparation of a Solid Composition ($Y_1$) Consisting of Arachidyl Alcohol, Behenyl Alcohol, Arachidyl Polyglucosides and Behenyl Polyglucoside The preparation method described in example 1.2 is carried out until the composition ($Y_1$) which is in the form of a nonpulverulent solid is obtained; the milling step is not performed. The analytical characteristics of the composition ($Y_1$) are indicated in table 1 below.

COMPARATIVE EXAMPLE 1.7

Preparation of a Solid Composition ($W_1$) Consisting of Lauryl Alcohol, Myristyl Alcohol, Cetyl Alcohol, Stearyl Alcohol, Arachidyl Alcohol, Behenyl Alcohol, Lauryl Polyglucosides, Myristyl Polyglucosides, Cetyl Polyglucosides, Stearyl Polyglucoside, Arachidyl Polyglucoside and Behenyl Polyglucosides The preparation method described in example 1.4 is carried out until the composition ($W_1$) which is in the form of a nonpulverulent solid is obtained; the milling step is not performed. The analytical characteristics of the composition ($W_1$) are indicated in table 1 below.

TABLE 1

Analytical characteristics of the compositions (X), (Y), ($X_1$), ($Y_2$), ($Y_1$), (W) and ($W_1$)

| | (X) | ($X_1$) | (Y) | ($Y_2$) | ($Y_1$) | (W) | ($W_1$) |
|---|---|---|---|---|---|---|---|
| Appearance at 20° C. (visual determination) | White powder | White solid | White powder | White powder | White solid | White powder | White solid |
| Acid number (NFT 60204) in mg of KOH/g | 0.3 | 0.3 | 0.25 | 0.24 | 0.25 | 0.27 | 0.27 |
| Hydroxyl number (USP XXI NF XVI Jan. 01, 1995) in mg of KOH/g | 214 | 214 | 273 | 298 | 273 | 245 | 245 |
| pH at 5% in water | 7.1 | 7.1 | 6.1 | 6.1 | 6.1 | 6.5 | 6.5 |
| Water (% by weight) (Standard NFT 73201) | 0.2 | 0.2 | 0.1 | 0.2 | 0.1 | 0.1 | 0.1 |
| Particle size Dv (90) in micrometers [2] | 29 | N.A.[1] | 64 | 100 | N.A.[1] | 118 | N.A.[1] |
| Residual alcohols (GC) in % by weight | 84.5 | 84.5 | 81.0 | 50.8 | 81.0 | 80.1 | 80.1 |

GC: (gas chromatography)
[1] N.A. = Not applicable
[2] The analytical characteristic Dv(90), which indicates the value of the mean diameter below which 90% of the volume of the particles of the pulverulent emulsifying composition exists, is measured using a Malvern Mastersizer 2000 laser particle sizer, equipped with an MS1-Small Volume Sample Dispersion dispersing device; the diluent used in this measurement is isopropyl myristate.

Principle of the Measurement of the Dv(90) Particle Size Technical Characteristic Using the Malvern Mastersizer 2000 Laser Particle Sizer Equipped with the MS1-Small Volume Sample Dispersion Dispersing Device The Malvern Mastersizer 2000 laser particle sizer uses the diffraction of a laser beam at a wavelength of 632 nanometers for measuring the size of the particles of the pulverulent composition analyzed. Generally, the small particles, present in the pulverulent composition to be analyzed, diffract the light of the laser beam with a low intensity but at a high angle; the large particles, present in the pulverulent composition to be analyzed, diffract the light of the laser beam with a strong intensity but at a low angle (according to Mie theory in Gustav Mie, "Beiträge zur Optik trüber Medien, speziell kolloidaler Metallösungen". Ann. Phys. Leipzig 25, 377-445 (1908); and according to the Franhofer approximation in Hecht, E., pages 396 and 397, (1987). Optics, 2nd edition. Addison Wesley. ISBN 0-201-11611-1). The Malvern Mastersizer 2000 laser particle sizer collects the light diffraction intensity as a function of the angle and links this information, by means of its software, to the size of the particles analyzed and present in the pulverulent composition.

Procedure for Measuring the Dv(90) Particle Size Technical Characteristic Using the Malvern Mastersizer 2000 Laser Particle Sizer Equipped with the MS1-Small Volume Sample Dispersion Dispersing Device A dispersion, comprising a content by volume of 0.0012% of pulverulent composition to be analyzed, in isopropyl myristate, is prepared by mixing the necessary volume of the pulverulent composition to be analyzed, into isopropyl myristate, in a beaker equipped with a magnetic stirrer. The dispersion thus prepared is then introduced into the MS1-Small Volume Sample Dispersion dispersing device equipped with a pump of which the rotational speed is set at 1500 rpm, so as to circulate this dispersion of the pulverulent composition to be analyzed in the measuring system of the Malvern Mastersizer 2000 laser particle sizer.

The operator then enters, into the interface of the measurement software of the Malvern Mastersizer 2000 laser particle sizer, the value of the refractive index of the isopropyl myristate, measured beforehand at the wavelength of the sodium D line (589.3 nanometers) and at 20° C., by means of an RE 40 refractometer sold by the company Mettler Toledo. During the measurement of the Dv(90) technical characteristic for the pulverulent emulsifying compositions (X), (Y), ($Y_2$) and (W) according to the invention, the refractive index of the isopropyl myristate, used as diluent for the requirements of the particle size measurements, determined at the wavelength of the sodium D line (589.3 nanometers) and at 20° C. using the RE 40 refractometer sold by the company Mettler Toledo, was measured at a value of 1.431.

At the end of the measurement, carried out according to the Franhofer approximation model, the Malvern Mastersizer 2000 laser particle sizer software provides several analytical characteristics of the pulverulent composition to be analyzed, including the Dv(90) analytical characteristic.

EXAMPLE 2

Preparation of Oil-in-Water Emulsions According to a Method Implementing a Step of Mixing the Pulverulent Emulsifying Composition According to the Invention into an Oily Phase A series of oil-in-water emulsions (emulsions E1 to E7), the compositions of which are indicated in tables 2 and 4 below, is prepared by carrying out, in the following method:
Step a):
The emulsifying composition to be tested is added to an oil introduced beforehand into a reactor brought to a temperature T1, and the mixture obtained is homogenized for 30 minutes by means of a stirrer fitted with an anchor spindle, at a speed of 80 rpm.
Step b):
The polyelectrolyte polymer is introduced into the mixture prepared at the end of step a), maintained at a temperature T1. The resulting mixture is homogenized for 15 minutes by means of a stirrer fitted with an anchor spindle, at a speed of 80 rpm.
Step c):
The water is introduced into the mixture prepared at the end of step b), and the resulting mixture is brought to a temperature T2, and then subjected to stirring by means of a rotor-stator emulsifying device, sold by the company Silverson, for a period of 4 minutes at a speed of 4000 rpm. The mixture resulting from step c) is then cooled to ambient temperature. Half the amount of each emulsion thus prepared is then stored in an insulated climatic chamber regulated at a temperature of 20° C., for 3 months. The other half of the amount of each emulsion thus prepared is stored in an insulated climatic chamber regulated at a temperature of 45° C., for 3 months. At the end of this 3-month period, the appearance of each emulsion prepared is observed.

The pulverulent emulsifying compositions (X), (Y), (Y$_2$) and (W) according to the invention and the solid emulsifying compositions (X$_1$), (Y$_1$) and (W$_1$) prepared in comparative examples 1.5, 1.6 and 1.7 were tested according to the method described above, at, for fatty phase preparation temperatures T1, 25° C., 40° C. and 60° C., and at emulsifying temperatures T2 of 25° C., 40° C. and 60° C.

TABLE 2

Composition and characterization of emulsions E1 to E7

| | % by weight Emulsion | | | | | | |
|---|---|---|---|---|---|---|---|
| Emulsifier | E1 | E2 | E3 | E4 | E5 | E6 | E7 |
| X | 2% | 0% | 0% | 0% | 0% | 0% | 0% |
| X$_1$ | 0% | 2% | 0% | 0% | 0% | 0% | 0% |
| Y | 0% | 0% | 2% | 0% | 0% | 0% | 0% |
| Y$_2$ | 0% | 0% | 0% | 2% | 0% | 0% | 0% |
| Y$_1$ | 0% | 0% | 0% | 0% | 2% | 0% | 0% |
| W | 0% | 0% | 0% | 0% | 0% | 2% | 0% |
| W$_1$ | 0% | 0% | 0% | 0% | 0% | 0% | 2% |
| Oil: C8-C10 triglyceride | 20% | 20% | 20% | 20% | 20% | 20% | 20% |
| SIMULGEL 600 (4) | 0.5% | 0.5% | 0.5% | 0.5% | 0.5% | 0.5% | 0.5% |
| Water | qs 100% | qs 100% | qs 100% | qs 100% | qs 100% | qs 100% | qs 100% |
| Sepicide ™ HB (3) | 1% | 1% | 1% | 1% | 1% | 1% | 1% |
| T1 (a) | 60° C. | 60° C. | 60° C. | 60° C. | 60° C. | 60° C. | 60° C. |
| T2 (b) | 60° C. | 60° C. | 60° C. | 60° C. | 60° C. | 60° C. | 60° C. |
| Appearance after 3 months at 20° C. | H (c) | Nf (d) | H | H | Nf | Nf | Nf |
| Appearance after 3 months at 45° C. | H | Nf | H | H | Nf | H | Nf |

(3) Sepicide ™ HB, which is a mixture of phenoxyethanol, methylparaben, ethylparaben, propylparaben and butylparaben, is a preservative sold by the company SEPPIC;
(4) SIMULGEL ™ 600 (acrylamide/sodium acryloyldimethyl taurate copolymer; isohexadecane; polysorbate 80) is a thickening and gelling composition sold by the company SEPPIC;
(a): T1 is the temperature for preparation of the emulsifier + oil mixture;
(b): T2 is the temperature for mixing the emulsion;
(c): H: homogeneous appearance
(d): Nf: emulsion not formed

TABLE 3

Composition and characterization of emulsions E8 to E14

| | % by weight Emulsions | | | | | | |
|---|---|---|---|---|---|---|---|
| Emulsifier | E8 | E9 | E10 | E11 | E12 | E13 | E14 |
| X | 2% | 0% | 0% | 0% | 0% | 0% | 0% |
| X$_1$ | 0% | 2% | 0% | 0% | 0% | 0% | 0% |
| Y | 0% | 0% | 2% | 0% | 0% | 0% | 0% |
| Y$_2$ | 0% | 0% | 0% | 2% | 0% | 0% | 0% |
| Y$_1$ | 0% | 0% | 0% v | 0% | 2% | 0% | 0% |

TABLE 3-continued

Composition and characterization of emulsions E8 to E14

| Emulsifier | % by weight Emulsions | | | | | | |
|---|---|---|---|---|---|---|---|
| | E8 | E9 | E10 | E11 | E12 | E13 | E14 |
| W | 0% | 0% | 0% | 0% | 0% | 2% | 0% |
| $W_1$ | 0% | 0% | 0% | 0% | 0% | 0% | 2% |
| Oil: C8-C10 triglyceride | 20% | 20% | 20% | 20% | 20% | 20% | 20% |
| SIMULGEL 600 | 0.5% | 0.5% | 0.5% | 0.5% | 0.5% | 0.5% | 0.5% |
| Water | qs 100% | qs 100% | qs 100% | qs 100% | qs 100% | qs 100% | qs 100% |
| Sepicide ™ HB | 1% | 1% | 1% | 1% | 1% | 1% | 1% |
| T1 (a) | 40° C. | 40° C. | 40° C. | 40° C. | 40° C. | 40° C. | 40° C. |
| T2 (b) | 40° C. | 40° C. | 40° C. | 40° C. | 40° C. | 40° C. | 40° C. |
| Appearance after 3 months at 20° C. | H (c) | Nf (d) | H | H | Nf | H | Nf |
| Appearance after 3 months at 45° C. | H | Nf | H | H | Nf | H | Nf |

(a): T1 is the temperature for preparing the emulsifier + oil mixture;
(b): T2 is the temperature for mixing the emulsion;
(c): H: homogeneous appearance
(d): Nf: emulsion not formed

TABLE 4

Composition and characterization of emulsions E15 to E21

| Emulsifier | % by weight Emulsions | | | | | | |
|---|---|---|---|---|---|---|---|
| | E15 | E16 | E17 | E18 | E19 | E20 | E21 |
| X | 2% | 0% | 0% | 0% | 0% | 0% | 0% |
| $X_1$ | 0% | 2% | 0% | 0% | 0% | 0% | 0% |
| Y | 0% | 0% | 2% | 0% | 0% | 0% | 0% |
| $Y_2$ | 0% | 0% | 0% | 2% | 0% | 0% | 0% |
| $Y_1$ | 0% | 0% | 0% v | 0% | 2% | 0% | 0% |
| W | 0% | 0% | 0% | 0% | 0% | 2% | 0% |
| $W_1$ | 0% | 0% | 0% | 0% | 0% | 0% | 2% |
| Oil: C8-C10 triglyceride | 20% | 20% | 20% | 20% | 20% | 20% | 20% |
| SIMULGEL 600 | 0.5% | 0.5% | 0.5% | 0.5% | 0.5% | 0.5% | 0.5% |
| Water | qs 100% | qs 100% | qs 100% | qs 100% | qs 100% | qs 100% | qs 100% |
| Sepicide ™ HB | 1% | 1% | 1% | 1% | 1% | 1% | 1% |
| T1 (a) | 25° C. | 25° C. | 25° C. | 25° C. | 25° C. | 25° C. | 25° C. |
| T2 (b) | 25° C. | 25° C. | 25° C. | 25° C. | 25° C. | 25° C. | 25° C. |
| Appearance after 3 months at 20° C. | H (c) | Nf (d) | H | H | Nf | H | Nf |
| Appearance after 3 months at 45° C. | H | Nf | H | H | Nf | H | Nf |

(a): T1 is the temperature for preparing the emulsifier + oil mixture;
(b): T2 is the temperature for mixing the emulsion;
(c): H: homogeneous appearance
(d): Nf: emulsion not formed The results included in tables 2 to 4 reveal that the use of the pulverulent emulsifying compositions (X), (Y), (Y₂) and (W) according to the invention makes it possible to obtain an oil-in-water emulsion which is stable during storage at 20° C. and at 45° C., by carrying out a preparation method according to the invention which is characterized by a temperature T1 of less than 70° C. during preparation of the fatty phase, and by a temperature T2 of less than 70° C. during the emulsification step.

The use of the comparative emulsifying compositions (X₁), (Y₁) and (W₁) which are in the form of undivided solids does not make it possible to obtain homogeneous oil-in-water emulsions by carrying out a preparation method according to the invention which is characterized by a temperature T1 of less than 70° C. during preparation of the fatty phase, and by a temperature T2 of less than 70° C. during the emulsification step.

Thus, for a temperature T1 for preparing the emulsifying system+oil mixture, which is fixed at 60° C., and for an emulsion mixing temperature T2 which is fixed at 60° C.:
- the emulsifying composition according to the invention (X) makes it possible to obtain a storage-stable homogeneous emulsion (E1), whereas the comparative emulsifying composition (X1) does not make it possible to form a stable homogeneous emulsion (E2);
- the emulsifying compositions according to the invention (Y) and (Y2) make it possible to obtain a storage-stable homogeneous emulsion (respectively, E3 and E4), whereas the comparative emulsifying composition (Y1) does not make it possible to form a stable homogeneous emulsion (E5);
- the emulsifying composition according to the invention (W) makes it possible to obtain a storage-stable homogeneous emulsion (E6), whereas the comparative emulsifying composition (W1) does not make it possible to form a stable homogeneous emulsion (E8).

The obtaining of storage-stable homogeneous emulsions through the use of the composition (X) according to the invention is also observed when the temperatures T1 and T2 are fixed, respectively, at 40° C. (E8) and at 25° C. (E15), whereas the use of the comparative emulsifying composition (X1) under the same conditions of temperature T1 and T2 does not make it possible to form a stable homogeneous emulsion (E9 and E16).

The obtaining of storage-stable homogeneous emulsions through the use of the compositions (Y) and (Y2) according to the invention is also observed when the temperatures T1 and T2 are fixed, respectively, at 40° C. (respectively, E10 and E11) and at 25° C. (respectively, E17 and E18), whereas the use of the comparative emulsifying composition (Y1) under the same conditions of temperature T1 and T2 does not make it possible to form a stable homogeneous emulsion (E12 and E19).

The obtaining of storage-stable homogeneous emulsions through the use of the composition (W) according to the invention is also observed when the temperatures T1 and T2 are fixed, respectively, at 40° C. (E13) and at 25° C. (E20), whereas the use of the comparative emulsifying composition (W1) under the same conditions of temperature T1 and T2 does not make it possible to form a stable homogeneous emulsion (E14 and E21).

EXAMPLE 3

Preparation of Oil-in-Water Emulsions According to a Method Implementing a Step of Mixing the Pulverulent Emulsifying Composition According to the Invention into an Aqueous Phase A series of oil-in-water emulsions, the compositions of which are indicated in table 5, is prepared by carrying out, in the following method:

Step a):

The emulsifying composition to be tested is added to an aqueous phase introduced beforehand into a reactor brought to a temperature T3, and the mixture obtained is homogenized for 30 minutes by means of a stirrer fitted with an anchor spindle, at a speed of 80 rpm.

Step b):

In parallel to step a), the polyelectrolyte polymer is introduced into an oil introduced beforehand into a separate reactor brought to the same temperature. The resulting mixture is homogenized for 15 minutes by means of a strirrer fitted with an anchor spindle, at a speed of 80 rpm.

Step c):

The aqueous phase comprising the emulsifying composition to be tested and prepared at the end of step a) is introduced into the mixture prepared at the end of step b), and the resulting mixture is brought to a temperature T4, and then subjected to stirring by means of a rotor-stator emulsifying device, sold by the company Silverson, for a period of 4 minutes at a speed of 4000 rpm. The mixture resulting from step c) is then cooled to ambient temperature. Half the amount of each emulsion thus prepared is then stored in an insulated climatic chamber regulated at a temperature of 20° C., for 3 months. The other half of the amount of each emulsion thus prepared is stored in an insulated climatic chamber regulated at a temperature of 45° C., for 3 months.

At the end of this 3-month period, the appearance of each emulsion prepared is observed.

The pulverulent emulsifying composition (X) according to the invention and the solid emulsifying composition ($X_1$) prepared in comparative example 1.5 were tested according to the method described above, at a fatty phase preparation temperature T3 of 60° C. and at an emulsifying temperature T4 of 60° C.

TABLE 5

Composition and characterization of emulsions E22 to E25

| Emulsifier | Emulsions | | | |
| --- | --- | --- | --- | --- |
| | E22 | E23 | E24 | E25 |
| X | 2% | 0% | 2% | 0% |
| $X_1$ | 0% | 2% | 0% | 2% |
| Water | qs 100% | qs 100% | qs 100% | qs 100% |
| Sepicide ™ HB[(3)] | 1% | 1% | 1% | 1% |
| Oil: C8-C10 triglyceride | 10% | 10% | 20% | 20% |
| SIMULGEL 600[(4)] | 0.5% | 0.5% | 0.5% | 0.5% |
| T3 (e) | 60° C. | 60° C. | 60° C. | 60° C. |
| T4 (f) | 60° C. | 60° C. | 60° C. | 60° C. |
| Appearance after 3 months at 20° C. | H | Nf | H | H |
| Appearance after 3 months at 45° C. | H | Nf | H | Nf |

(c): H: homogeneous appearance
(d): Nf: emulsion not formed
(e): T3 is the temperature for preparing the emulsifier + aqueous phase mixture;
(f): T4 is the temperature for mixing the emulsion The results included in table 5 reveal that the use of the pulverulent emulsifying composition (X) according to the invention makes it possible to obtain oil-in-water emulsions comprising weight proportions of 10% and 20% of oil, which are stable and homogeneous during storage at 20° C. and at 45° C., by carrying out a preparation method according to the invention which is characterized by a temperature T3 of 60° C. during preparation of the aqueous phase, and by a temperature T4 of 60° C. during the emulsification step (emulsions E22 and E24).

The use of the comparative emulsifying composition ($X_1$) which is in the form of a nonpulverulent solid does not make it possible to obtain oil-in-water emulsions comprising weight proportions of 10% and 20% of oil, by carrying out a preparation method according to the invention which is characterized by a temperature T3 of 60° C. during preparation of the aqueous phase, and by a temperature T4 of 60° C. during the emulsification step (emulsions E23 and E25).

EXAMPLE 4

Preparation of a Self-Tanning Oil-in-Water Emulsion According to a Method Implementing a Step of Mixing the Pulverulent Emulsifying Composition According to the Invention into an Aqueous Phase Dihydroxyacetone is a product commonly used in the cosmetics industry as an agent for artificial tanning and/or browning of the skin; applied to the latter, it makes it possible to obtain a tanning or browning effect having an appearance more or less similar to that which can result from prolonged exposure to the sun or under an ultraviolet radiation lamp. Dihydroxyacetone has the drawback of being degraded when it is used at temperatures above 70° C., which generally results in undesired yellowing of the compositions which contain it.

4.1

A series of oil-in-water emulsions comprising dihydroxyacetone and the emulsifying compositions to be tested, the compostions of which are indicated in table 6, is prepared by carrying out, in the following method:

Step a):

The emulsifying composition to be tested is added to an oil introduced beforehand into a reactor brought to a temperature T5, and the mixture obtained is homogenized for 30 minutes by means of a stirrer fitted with an anchor spindle, at a speed of 50 rpm.

Step b):

In parallel to step a), an aqueous phase comprising dihydroxyacetone is prepared in a separate reactor brought to a temperature of 25° C. The resulting mixture is homogenized for 15 minutes by means of a stirrer fitted with an anchor spindle, at a speed of 50 rpm.

Step c):

The aqueous phase prepared at the end of step b) and a polyelectrolyte polymer are jointly added to the fatty phase comprising the emulsifying composition to be tested and prepared at the end of step a) at a temperature T6, and then the resulting mixture is subjected to stirring by means of a rotor-stator emulsifying device, sold by the company Silverson, for a period of 4 minutes at a speed of 3000 rpm. The mixture resulting from step c) is then cooled to ambient temperature. The emulsions prepared are then stored in an insulated climatic chamber regulated at a temperature of 20° C., for 7 days. At the end of this 7-day period, the appearance of the emulsion prepared is observed and the change in the coloration thereof (ΔE) as described below is measured using a Minolta CR200 chromameter.

4.2 Principle of the Method for Measuring the Color of a Cosmetic Composition The change in the coloration of compositions comprising dihydroxyacetone is estimated by comparing over time a numerical characteristic ΔE, calculated from the measurement of 3 constituent parameters of a color:

- the L* parameter, ranging between 0 and 100, which represents the lightness of the shade, the higher the value, the lighter the shade;
- the a* parameter, which ranges from −60 to +60, and expresses the entire range from green (a*=−60) to red (a*=+60);
- the b* parameter, which ranges from −60 to +60, and expresses the entire range from blue (b*=−60) to yellow (b*=+60).

The L*, a* and b* parameters, characterizing an oil-in-water emulsion comprising dihydroxyacetone, are measured for the various oil-in-water emulsions prepared at a temperature of 25° C., and then the ΔE value is therefore calculated as follows:

$$\Delta E = \sqrt{((\Delta L^*)^2 + (\Delta a^*)^2 + (\Delta b^*)^2)},$$

with:

ΔL*=L* at t2−L* at t1
Δa*=a* at t2−a* at t1
Δb*=a* at t2−b* at t1

4.3 Experimental Results

The compositions of each emulsion E20 and E21 are indicated in table No. 6 hereinafter, as is the characterization of their appearance and of the change in their coloration (ΔE) after storage for 7 days at 25° C. The constituent parameters L*, a* and b* of the color of each emulsion are measured with a Minolta CR200 chromameter sold by the company Minolta, so as to measure the corresponding ΔE value.

TABLE 6

Composition and characterization of emulsions E26 and E27

| Emulsifier | Emulsions | |
|---|---|---|
| | E26 | E27 |
| X | 2% | 0% |
| X₁ | 0% | 2% |
| Oil phase | | |
| C12-C15 alkyl benzoate | 10% | 10% |
| Dimethicone DC 200/350 (5) | 5% | 5% |
| Tocopherol | 0.05% | 0.05% |
| Sepicide ™ HB | 1.0% | 1.0% |
| Simulgel ™ INS 100 (6) | 1.0% | 1.0% |
| Aqueous phase | | |
| Glycerol | 3.0% | 3.0% |
| Propylene glycol | 2.0% | 2.0% |
| Water | qs 100% | qs 100% |
| Citric acid | qs pH 4 | qs pH 4 |
| Self-tanning agent | | |
| Dihydroxyacetone in solution at 50% in water | 5.0% | 5.0% |
| T5 (g) | 40° C. | 80° C. |
| T6 (h) | | |
| Appearance of the emulsions after 7 days at 25° C. | Homogeneous emulsion | Homogeneous emulsion |
| ΔE after 7 days at 25° C. | 27.0 | 4.2 |

(5) DC 200/350 is a cyclomethicone sold by the company Dow Corning.
(6) Simulgel ™ INS 100 (hydroxyethyl acrylate/sodium acryloyldimethyl taurate copolymer; isohexadecane; polysorbate 60) is a thickening and gelling composition sold by the company SEPPIC.

(g): T5 is the temperature for preparing the emulsifying system+oily phase mixture.
(h): T6 is the temperature for mixing the emulsion.

The results recorded in table 6 reveal that the oil-in-water emulsion E26 comprising dihydroxyacetone, prepared with the composition (X) according to the invention, by carrying out a preparation method according to the invention which is characterized by a temperature T5 of 40° C. during step a) of preparing the fatty phase, and by a temperature T6 of 40° C. during emulsification step c), creates a reduced change in coloration after storage for 7 days at a temperature of 25° C., compared with the comparative emulsion E27 prepared with the comparative emulsifying composition (X₁), using a preparation method which is characterized by a temperature T5 of 80° C. during step a) of preparing the fatty phase, and by a temperature T6 of 80° C. during emulsification step c). Thus, the value of the ΔE characteristic after 7 days of storage at a temperature of 25° C. is 27.0 for the comparative emulsion E27 and 4.2 for the emulsion E26 using the pulverulent emulsifying composition (X) according to the invention and the preparation method according to the invention which is characterized by a temperature T5 of 40° C. during step a) for preparing the fatty phase, and by a temperature T6 of 40° C. during emulsification step c).

EXAMPLE 5

Preparation of an Oil-in-Water Emulsion Comprising a Volatile Oil According to a Method Implementing a Step of Mixing the Pulverulent Emulsifying Composition According to the Invention into an Oily Phase A series of oil-in-water emulsions comprising a volatile silicone oil, namely the cyclomethicone DC245 sold by the company Dow Corning, and the emulsifying compositions to be tested, the compositions by weight of which are indicated in table 7 for a total theoretical weight (thWt) of emulsion of 1000 grams, is prepared by carrying out, in the following method:

Step a):

The emulsifying composition to be tested is added to an oil introduced beforehand into a beaker with a volume of 2 liters and brought to a temperature T7, and the mixture obtained is homogenized for 30 minutes by means of a stirrer fitted with an anchor spindle, at a speed of 80 rpm.

Step b):

The polyelectrolyte polymer and the water are introduced concomitantly into the mixture prepared at the end of step a), maintained at a temperature T7. The resulting mixture is subjected to stirring by means of a rotor-stator emulsifying device, sold by the company Silverson, for a period of 5 minutes at a speed of 3000 rpm and at a temperature T8. The mixture resulting from step b) is then cooled to ambient temperature and weighed so as to determine the weight Wt1 of emulsion prepared.

The yield (Yld) from preparation of the emulsion, expressed as a percentage, is calculated as follows:

$$\text{Yield}(Yld) = (Wt1 \times 100)/thWt$$

Half the amount of each emulsion thus prepared is then stored in an insulated climatic chamber regulated at a temperature of 20° C., for 3 months. The other half of the amount of each emulsion thus prepared is stored in an insulated climatic chamber regulated at a temperature of 45° C., for 3 months. At the end of this 3-month period, the appearance of each emulsion prepared is observed.

TABLE 7

Composition and characterization of emulsions E28 and E29

|  | Emulsion E28 | Emulsion E29 |
|---|---|---|
| Emulsifying system | | |
| Composition (W) | 3% | 0% |
| Composition ($W_1$) | 0% | 3% |
| Oil: Cyclomethicone DC 245[7] | 20% | 20% |
| Simulgel ™ INS 100[6] | 0.5% | 0.5% |
| Water | qs 100% | qs 100% |
| T7(i) | 40° C. | 80° C. |
| T8(j) | 40° C. | 80° C. |
| Theoretical weight thWt | 1000 g | 1000 g |
| Weight Wt1 of emulsion prepared | 991 g | 903 g |
| Yield (Yld) | 99.1% | 90.3% |
| Appearance after 3 months at 20° C. | Homogeneous emulsion | Homogeneous emulsion |
| Appearance after 3 months at 45° C. | Homogeneous emulsion | Homogeneous emulsion |

[7]DC 245 is a cyclomethicone sold by the company Dow Corning.
(i): T7 is the temperature for preparing the emulsifying system + oil phase mixture.
(j): T8 is the temperature for mixing the emulsion.

The results recorded in table 7 reveal that the oil-in-water emulsion E28 comprising the volatile oil DC 245, prepared with the composition (W) according to the invention, by carrying out a preparation method according to the invention which is characterized by a temperature T7 of 40° C. during step a) of preparing the fatty phase, and by a temperature T8 of 40° C. during emulsification step b), is characterized by an emulsion preparation yield by weight of 99.1%, whereas the comparative emulsion E29, prepared with the comparative composition ($W_1$), by carrying out a preparation method which is characterized by a temperature T7 of 80° C. during step a) of preparing the fatty phase, and by a temperature T8 of 80° C. during emulsification step b), is characterized by an emulsion preparation yield by weight of 90.1%.

The composition (W) according to the invention thus makes it possible to prepare a water-in-oil emulsion comprising a volatile phase with a better yield by weight, and while reducing the losses of volatile oil owing to evaporation during the implementation of the method for preparing the oil-in-water emulsion.

Formulations

In the following formulations, the percentages are expressed as percentage by weight for 100% of the weight of the formulation.

EXAMPLE 6

Care Cream

| | |
|---|---|
| Cyclomethicone: | 10% |
| Simulgel ™ EG: | 0.8% |
| Composition (Y): | 2% |
| Stearyl alcohol: | 1% |
| Stearic alcohol: | 0.5% |
| Preservative: | 0.65% |
| Lysine: | 0.025% |
| EDTA (disodium salt): | 0.05% |
| Xanthan gum: | 0.2% |
| Glycerol: | 3% |
| Water: | qs 100% |

EXAMPLE 7

Antisun Milk

FORMULA

| | | |
|---|---|---|
| A | Composition (Y): | 3.0% |
|  | Sesame oil: | 5.0% |
|  | PARSOL ™ MCX: | 5.0% |
|  | λ Carrageenan: | 0.10% |
| B | Water: | qs 100% |
| C | Simulgel ™ NS: | 0.80% |
| D | Fragrance: | qs |
|  | Preservative: | qs |

PROCEDURE

B is emulsified in A at 60° C. and then C is added at about 60° C., followed by D at about 30° C., and the pH is adjusted if necessary.

EXAMPLE 8

Moisturizing and Matting Foundation

FORMULA

| | | |
|---|---|---|
| A | Water: | 20.0% |
|  | Butylene glycol: | 4.0% |
|  | PEG-400: | 4.0% |
|  | Pecosil ™ PS100: | 1.0% |
|  | Sodium hydroxide: | qs pH = 9 |
|  | Titanium dioxide: | 7.0% |
|  | Talc: | 2.0% |
|  | Yellow iron oxide: | 0.8% |
|  | Red iron oxide: | 0.3% |
|  | Black iron oxide: | 0.05% |

-continued

| FORMULA | | |
|---|---|---|
| B | Lanol ™ 99: | 8% |
| | Caprylic/capric triglyceride | 8% |
| | Composition (X): | 5.00% |
| C | Water: | qs 100% |
| | Micropearl ™ M305: | 2.0% |
| | Tetrasodium EDTA: | 0.05% |
| D | Cyclomethicone: | 4.0% |
| | Xanthan gum: | 0.2% |
| | Simulgel ™ EG: | 2.5% |
| E | Sepicide ™ HB: | 0.5% |
| | Sepicide CI: | 0.3% |
| | Fragrance: | 0.2% |

PROCEDURE

Mixtures B+D and A+C are prepared at 60° C., and then mixed together and the whole is emulsified.

EXAMPLE 9

Body Milk

| Composition (Y): | 3.5% |
|---|---|
| Lanol ™ 37T: | 8.0% |
| Solagum ™ L: | 0.05% |
| Water: | qs 100% |
| Benzophenone-3: | 2.0% |
| Dimethicone 350 cPs: | 0.05% |
| Simulgel ™ NS: | 2.5% |
| Preservative: | 0.2% |
| Fragrance: | 0.4% |

EXAMPLE 10

Makeup-Removing Emulsion with Sweet Almond Oil

| Composition (Y2): | 5% |
|---|---|
| Sweet almond oil: | 5% |
| Water: | qs 100% |
| Simulgel ™ INS 100: | 0.3% |
| Glycerol: | 5% |
| Preservative: | 0.2% |
| Fragrance: | 0.3% |

EXAMPLE 11

Moisturing Cream for Greasy Skin

| Composition (Y): | 5% |
|---|---|
| Cetyl stearyl octanoate: | 8% |
| Octyl palmitate: | 2% |
| Water: | qs 100% |
| Simulgel ™ NS: | 2.6% |
| Micropearl ™ M100: | 3.0% |
| Mucopolysaccharides: | 5% |
| Sepicide ™ HB: | 0.8% |
| Fragrance: | 0.3% |

EXAMPLE 12

Cream with AHAs for Sensitive Skin

| Mixture of N-laurylamino acids: | 0.1% to 5% |
|---|---|
| Magnesium potassium aspartate: | 0.002% to 0.5% |
| Lanol ™ 99: | 2% |
| Composition (Y): | 5.0% |
| Water: | qs 100% |
| Simulgel ™ NS: | 1.50% |
| Gluconic acid: | 1.50% |
| Triethanolamine (TEA): | 0.9% |
| Sepicide ™ HB: | 0.3% |
| Sepicide ™ CI: | 0.2% |
| Fragrance: | 0.4% |

EXAMPLE 13

Make-Up Removing Milk

| Composition (X): | 3% |
|---|---|
| Primol ™ 352: | 8.0% |
| Sweet almond oil: | 2% |
| Water: | qs 100% |
| Simulgel ™ NS: | 0.8% |
| Preservative: | 0.2% |

EXAMPLE 14

Antisun Milk

| Composition (Y): | 3.5% |
|---|---|
| Lanol ™ 37T: | 10.0% |
| Parsol ™ MCX: | 5.0% |
| Eusolex ™ 4360: | 2.0% |
| Water: | qs 100% |
| Sepiplus ™ 400: | 1.8% |
| Preservative: | 0.2% |
| Fragrance: | 0.4% |

EXAMPLE 15

Cream with AHAs

| Composition (Y): | 5.0% |
|---|---|
| Deepaline ™ PVB: | 1.05% |
| Lanol ™ 99: | 10.0% |
| Water: | qs 100% |
| Gluconic acid: | 1.5% |
| TEA (triethanolamine): | 0.9% |
| Simulgel ™ NS: | 1.5% |
| Fragrance: | 0.4% |
| Sepicide ™ HB: | 0.2% |
| Sepicide ™ CI: | 0.4% |

EXAMPLE 16

Self-Taning Emulsion

| | |
|---|---|
| Lanol ™ 99: | 15% |
| Composition (Y): | 5.0% |
| Parsol ™ MCX: | 3.0% |
| Water: | qs 100% |
| Dihydroxyacetone: | 5.0% |
| Monosodium phosphate: | 0.2% |
| Simulgel ™ NS: | 2.5% |
| Fragrance: | 0.3% |
| Sepicide ™ HB: | 0.8% |
| Sodium hydroxide: | qs pH = 5. |

EXAMPLE 17

Care Cream

| | |
|---|---|
| Cyclomethicone: | 10% |
| Simulgel ™ EG: | 2.8% |
| Composition (Y): | 4.5% |
| Preservative: | 0.65% |
| Lysine: | 0.025% |
| EDTA (disodium salt): | 0.05% |
| Xanthan gum: | 0.2% |
| Glycerol: | 3% |
| Water: | qs 100% |

EXAMPLE 18

Care Cream

| | |
|---|---|
| Cyclomethicone: | 10% |
| Sepigel ™ 305: | 0.8% |
| Composition (Y): | 4.5% |
| Perfluoropolymethyl isopropyl ether: | 0.5% |
| Preservative: | 0.65% |
| Lysine: | 0.025% |
| EDTA (disodium salt): | 0.05% |
| Pemulen ™ TR1: | 0.2% |
| Glycerol: | 3% |
| Water: | qs 100% |

EXAMPLE 19

Body Milk

| | | |
|---|---|---|
| | FORMULA | |
| A | Composition (Y2): | 3.0% |
| | Glyceryl triheptonate: | 10.0% |
| B | Water: | qs 100% |
| C | Simulgel ™ EG: | 1.0% |
| D | Fragrance: | qs |
| | Preservative: | qs |

PROCEDURE

A is melted at approximately 40° C. B is emulsified in A at 40° C. and then C is added at about 40° C., followed by D.

EXAMPLE 20

Body Milk

| | |
|---|---|
| Composition (Y): | 3.5% |
| Lanol ™ 37T: | 8.0% |
| Solagum ™ L: | 0.05% |
| Water: | qs 100% |
| Benzophenone-3: | 2.0% |
| Dimethicone 350 cPs: | 0.05% |
| Simulgel ™ NS: | 2.8% |
| Preservative: | 0.2% |
| Fragrance: | 0.4% |

EXAMPLE 21

Cream with AHAs

| | |
|---|---|
| Composition (Y): | 5.0% |
| Deepaline ™ PVB: | 1.05% |
| Lanol ™ 99: | 10.0% |
| Water: | qs 100% |
| Gluconic acid: | 1.5% |
| TEA (triethanolamine): | 0.9% |
| Simulgel ™ EG: | 1.5% |
| Fragrance: | 0.4% |
| Sepicide ™ HB: | 0.2% |
| Sepicide ™ CI: | 0.4% |

EXAMPLE 22

Makeup-Removing Milk

| | |
|---|---|
| Simulsol ™ 165: | 4% |
| Composition (Y2): | 1% |
| Caprylate/caprate triglyceride: | 15% |
| Pecosil ™ DCT: | 1% |
| Demineralized water: | qs |
| Capigel ™ 98: | 0.5% |
| Simulgel ™ INS 100: | 1% |
| Proteol ™ APL: | 2% |
| Sodium hydroxide: | qs pH = 7 |

EXAMPLE 23

Antisun Cream

| | |
|---|---|
| Simulsol ™ 165: | 3% |
| Composition (Y): | 2% |
| C12-C15 benzoate: | 8% |
| Pecosil ™ PS 100: | 2% |
| Dimethicone: | 2% |
| Cyclomethicone: | 5% |
| Octyl para-methoxycinnamate: | 6% |
| Benzophenone-3: | 4% |
| Titanium oxide: | 8% |

-continued

| | |
|---|---|
| Xanthan gum: | 0.2% |
| Butylene glycol: | 5% |
| Demineralized water: | qs 100% |
| Simulgel ™ NS: | 1.5% |
| Preservative, fragrance: | qs |

EXAMPLE 24

Vitamin-Containing Cream

| | |
|---|---|
| Simulsol ™ 165: | 5% |
| Composition (Y): | 1% |
| Caprylic/capric triglycerides: | 20% |
| Vitamin A palmitate: | 0.2% |
| Vitamin E acetate: | 1% |
| Micropearl ™ M 305: | 1.5% |
| Simulgel ™ 600: | 2% |
| Water | qs 100% |
| Preservative, fragrance | qs |

EXAMPLE 25

Antisun Self-Tanning Gel

| | |
|---|---|
| Composition (Y): | 3.0% |
| Glyceryl triheptanoate: | 10.0% |
| Deepaline ™ PVB: | 1.05% |
| Simulgel ™ EG: | 2.2% |
| Water: | qs 100% |
| Dihydroxyacetone: | 5% |
| Fragrance: | 0.1% |
| Sepicide ™ HB: | 0.3% |
| Sepicide ™ CI: | 0.1% |
| Parsol ™ MCX: | 4.0% |

EXAMPLE 26

Self-Tanning Cream Containing α-hydroxy Acids

| | |
|---|---|
| Composition (Y): | 5.0% |
| Deepaline ™ PVB: | 1.05% |
| Lanol ™ 99: | 10.0% |
| Water: | qs 100% |
| Gluconic acid: | 1.5% |
| Dihydroxyacetone: | 3% |
| Triethanolamine: | 0.9% |
| Simulgel ™ EG: | 1.5% |
| Fragrance: | 0.4% |
| Sepicide ™ HB: | 0.2% |
| Sepicide ™ CI: | 0.4% |

EXAMPLE 27

Self-Tanning Cream Containing α-hydroxy Acids for Sensitive Skin

| | |
|---|---|
| Mixture of N-lauroylamino acids: | 0.1% to 5% |
| Magnesium potassium aspartate: | 0.002% to 0.5% |
| Composition (X): | 5.0% |
| Lanol ™ 99: | 2.0% |
| Water: | qs 100% |

-continued

| | |
|---|---|
| Lactic acid: | 1.5% |
| Dihydroxyacetone: | 3.5% |
| Triethanolamine: | 0.9% |
| Simulgel ™ NS: | 1.5% |
| Fragrance: | 0.4% |
| Sepicide ™ HB: | 0.3% |
| Sepicide ™ CI: | 0.2% |

The definitions of the commercial products used in the examples are as follows:

Capigel™ 98 is a liquid thickener based on an acrylate copolymer, sold by the company SEPPIC.

Lanol™ 99 is isononyl isononanoate sold by the company SEPPIC.

Micropearl™ M 100 is an ultrafine powder with a very soft feel and a matting action, sold by the company Matsumo.

Sepicide™ CI, imidazolidineurea, is a preservative sold by the company SEPPIC.

Pemulen™ TR1 is an acrylic polymer sold by Goodrich.

Simulsol™ 165 is self-emulsifying glyceryl stearate sold by the company SEPPIC.

Sepicide™ HB, which is a mixture of phenoxyethanol, methylparaben, ethylparaben, propylparaben and butylparaben, is a preservative sold by the company SEPPIC.

Parsol™ MCX is octyl para-methoxy cinnamate, sold by the company Givaudan.

Lanol™ 37T is glyceryl triheptanoate, sold by the company SEPPIC.

Solagum™ L is a carrageenan sold by the company SEPPIC.

Eusolex™ 4360 is a sunscreen sold by the company Merck.

Deepaline™ PVB is an acylated wheat protein hydrolysate sold by the company SEPPIC.

Proteol™ APL is a foaming surfactant sold by the company SEPPIC.

Micropearl™ M 305 is a silky water-dispersible powder based on crosslinked methyl methacrylate copolymer.

Simulgel™ EG: self-inversible inverse latex of copolymer such as those described in international publication WO 99/36445 (INCI name: sodium acrylate/sodium acryloyldimethyl taurate copolymer and isohexadecane and polysorbate 80), sold by the company SEPPIC.

Sepiplus™ 400: self-inversible inverse latex of copolymers such as those described in international publication WO 2005/040230 (INCI name: Polyacrylate-13 & Polyisobutene & Polysorbate 20), sold by the company SEPPIC.

Simulgel™ NS: self-inversible inverse latex of thickening copolymers (INCI name: hydroxyethyl acrylate/sodium acryloyldimethyl taurate copolymer and squalane and Polysorbate 60), sold by the company SEPPIC.

Simulgel™ INS 100: self-inversible inverse latex of thickening copolymers (INCI name: hydroxyethyl acrylate/sodium acryloyldimethyl taurate copolymer and isohexadecane and Polysorbate 60), sold by the company SEPPIC.

Simulgel™ 600: self-inversible inverse latex of thickening copolymers (INCI name: acrylamide/sodium acryloyldimethyl taurate copolymer and isohexadecane and Polysorbate 80), sold by the company SEPPIC.

Sepigel™ 305: self-inversible inverse latex of thickening copolymers (INCI name: polyacrylamide and C13-C14 isoparaffin and Laureth-7), sold by the company SEPPIC.

Primol™ 352 is a mineral oil sold by the company Exxon.

Pecosil™ DCT is sodium dimethicone PEG-7 acetyl methyl taurate sold by the company Phoenix.

Pecosil™ PS 100 is dimethicone PEG-7 sold by the company Phoenix.

The invention claimed is:

1. A pulverulent composition C1 comprising:
   (i) at least one compound of formula (I):

$$R\text{—}O\text{-}(G)_x\text{-}H \quad (I)$$

in which the R radical represents a saturated linear aliphatic radical containing from 16 to 18 carbon atoms, G represents the residue of a reducing sugar selected from the group consisting of glucose, xylose and arabinose, and x represents a decimal number greater than or equal to 1 and less than or equal to 10; and
   (ii) one or more alcohols of formula (II):

$$R'\text{—}OH \quad (II)$$

In which the R' radical, which may be identical to or different than the R radical as defined above, represents a saturated linear aliphatic radical containing from 16 to 18 carbon atoms,
   wherein at least 90% by volume of particles in said pulverulent composition have a diameter of less than or equal to 250 micrometers, and
   wherein the pulverulent composition C1 comprises, for 100% of its weight:
   from 5% by weight to 20% by weight of at least one compound of formula (Ia), corresponding to formula (I) in which R represents a saturated linear aliphatic radical containing from 20 to 22 carbon atoms;
   from 1.5% by weight to 10% by weight of at least one compound of formula (Ib) corresponding to formula (I) as defined above, in which R represents a saturated linear aliphatic radical containing from 12 to 14 carbon atoms;
   from 1% by weight to 10% by weight of at least one compound of formula (Ic) corresponding to formula (I) as defined above, in which R represents a saturated linear aliphatic radical containing from 16 to 18 carbon atoms;
   from 45% by weight to 80% by weight of at least one compound of formula (IIa) corresponding to formula (II) as defined above, in which R' represents a saturated linear aliphatic radical containing from 20 to 22 carbon atoms;
   from 5% by weight to 10% by weight of at least one compound of formula (IIb) corresponding to formula (II) as defined above, in which R' represents a saturated linear aliphatic radical containing from 12 to 14 carbon atoms; and
   from 0% by weight to 10% by weight of at least one compound of formula (IIc) corresponding to formula (II) as defined above, in which R' represents a saturated linear aliphatic radical containing from 16 to 18 carbon atoms.

2. The pulverulent composition C1 as defined in claim 1, in which at least 90% by volume of the particles have a diameter of less than or equal to 100 micrometers.

3. An oil-in-water cosmetic emulsion comprising an effective amount of pulverulent composition C1 as defined in claim 1 as an emulsifier to stabilize said oil-in-water emulsion.

4. The emulsion according to claim 3, wherein said effective amount is between 1% by weight and 10% by weight of the total weight of the emulsion.

5. The emulsion according to claim 3, wherein the emulsion is of a form selected from the group consisting of an oil-in-water emulsion, a water-in-oil emulsion, a water-in-oil-in-water emulsion and an oil-in-water-in-oil emulsion.

6. The emulsion according to claim 5, wherein the emulsion is an oil-in-water emulsion comprising a cosmetically acceptable aqueous phase.

* * * * *